United States Patent [19]

Knapp et al.

[11] 3,966,332

[45] June 29, 1976

[54] METHOD AND APPARATUS FOR INSPECTING LIQUIDS IN TRANSPARENT CONTAINERS

[75] Inventors: Julius Z. Knapp, Somerset; John C. Zeiss, Bloomfield, both of N.J.

[73] Assignee: Schering Corporation, Kenilworth, N.J.

[22] Filed: Sept. 12, 1974

[21] Appl. No.: 505,431

[52] U.S. Cl. ............................ 356/197; 250/223 B; 356/240
[51] Int. Cl.² .................................... G01N 21/24
[58] Field of Search ........... 356/196, 197, 198, 239, 356/240; 250/227, 222 PC, 223 B; 209/111.7

[56] References Cited
UNITED STATES PATENTS

| | | | |
|---|---|---|---|
| 2,132,447 | 10/1938 | Stout | 250/223 B |
| 2,323,636 | 7/1943 | Weathers | 209/111.7 |
| 3,029,349 | 4/1962 | Schell | 250/223 B |
| 3,292,785 | 12/1966 | Calhoun | 356/240 |
| 3,576,442 | 4/1971 | Nakamura | 356/197 |
| 3,627,423 | 12/1971 | Knapp et al. | 356/197 |
| 3,639,067 | 2/1972 | Stephens | 356/240 |
| 3,777,169 | 12/1973 | Walter et al. | 356/240 |

*Primary Examiner*—Vincent P. McGraw
*Attorney, Agent, or Firm*—Vincent H. Gifford; Bruce M. Eisen; Stephen B. Coan

[57] ABSTRACT

A method and apparatus for automatically inspecting liquid filled containers for particulate contaminants in relative size. The method comprising the steps of illuminating the liquid with a constant intensity light source, dissecting the image of the entire illuminated liquid volume, including the meniscus, with fiber optic bundles and monitoring the fiber optic bundles with an array of constant sensitivity photo sensors. Each photo sensor continually translates the illumination value of an assigned and separate cross sectional unit area of the vial image into a voltage signal and monitors each signal for a signal change indicative of particulate movement. The interfering output signal due to the meniscus decay is corrected, and the accept-/reject decision is based upon a composite signal representative of all the differentiated signals received from the array of photo sensors.

37 Claims, 11 Drawing Figures

METHOD AND APPARATUS FOR INSPECTING LIQUIDS IN TRANSPARENT CONTAINERS

FIELD OF THE INVENTION

This invention relates to a method and apparatus for inspecting liquid filled transparent containers for particulate contamination, especially such method and apparatus for detecting the presence of particulate matter in ampoules, bottles, flasks, syringes or vials.

BACKGROUND OF THE INVENTION

The art of inspecting liquid filled containers, especially vials and ampoules, for the presence of pariculate matter is a relatively old and crowded one as exemplified by U.S. Pat. Nos. 2,132,447 (Stout); 2,426,355 (Kellogg); 2,531,529 (Price); 3,029,349 (Schell); 3,217,877 (Honjyo et al); 3,292,785 (Calhoun); 3,415,997 (Vinzelberg et al); 3,496,369 (Makino et al); 3,528,544 (Noguchi et al); 3.598,907 (Drinkuth); 3,627,423 (Knapp et al); 3,777,169 (Walter et al); and 3,914,058 (Knapp). In each of the foregoing U.S. Patents, and also in the present case, the inspection process includes the steps of rotating a container to be inspected, suddenly stopping the rotation of the container, and then inspecting the illuminated rotating fluid for moving particles. This simplifies detection of particles since a moving illuminated particle can be easily detected and is readily distinguishable from the stationary reflection which results from container imperfections.

Many prior art systems have been developed which inspect liquid filled transparent containers with photo sensors for both large particles (e.g. glass fragments) and fine particulate matter (below 50 microns). The rotating liquid eddy or vortex produces a change in the illumination signal, which is indistinguishable from a moving particle signal. The prior art systems therefore had to wait for the vortex to disappear before the photo sensor could make an accurate reading of particulate movement. However, when small particles are present, there is a considerable possibility that they will rise to the meniscus and be flung to the wall of the container by centrifugal force, where they could cling and thereby avoid detection. The prior art systems, as for example, U.S. Pat. No. 2,531,529, were able to eliminate the effect of the vortex signal by blocking it until it was no longer appreciable. However, none of the prior art systems recognized that the interference due to the vortical meniscus decay at the liquid-container interface could be corrected thereby allowing a faster and more accurate inspection of the rotating meniscus.

Prior art systems have generally used only one or two photo sensors each of which are directed at the entire rotating solution, or as in U.S. Pat. No. 2,132,447 a plurality of photo sensors aligned in the vertical direction to allow different portions of the container to be given preferential treatment. If specular reflections from either the surface of the liquid or optical flaws in the container are of sufficient intensity, a photo sensor could saturate at its peak current. If this occurred, it would be impossible to detect any change in illumination due to particle movement at the liquid volume which was monitored by that photo sensor. Since the movement of the particles is a strongly horizontal one, if one of the vertically aligned photo sensors was so saturated, any particle in the liquid zone of that particular photo sensor would be missed.

An advantage of the invention is to provide an improved system which can inspect the entire liquid in a transparent container including the rotating meniscus for particulate contamination in a faster and more reliable manner than previous methods.

A further advantage of the invention is to provide an improved system which can inspect a liquid in a transparent container for particulate contamination with the same sensitivity independent of the container size and specular reflections from marks and defects in the container.

SUMMARY OF THE INVENTION

In the method and apparatus of the instant invention, the container to be inspected is illuminated by a source of radiant energy. Any source of radiant energy such as single or multiple optical glass fiber bundles which are used in U.S. Pat. No. 3,627,423, or ultraviolet or infrared light could be used. The preferred mode of illumination is as described in the above noted U.S. Pat. No. 3,627,423 to Knapp et al, which is herein incorporated by reference. A means to hold the light source at a constant intensity is desirable, however, whenever a calibrated size response is needed, as in any parenteral drug inspection in which relative size of the particulate matter is of importance.

The liquid filled container is rotated at a speed sufficient to rotate the liquid and any particles therein, but below the condition that will cause cavitation and bubbling of the liquid. The rotation of the container is then suddenly stopped. The rays emanating from the radiation source strike the internal surface of the container and are directed towards the particles moving in the solution, thereby illuminating the particles. The illumination signal generated by the moving particles is distinguished from the constant illumination signal generated by stationary scratches, flaws, stains or other optical defects in the walls of the container or by particles, dust, lettering or art work that may be on the outside of the container. The rotation of the container is preferably about a vertical axis giving any particles therein a strongly horizontal motion. It is, of course, recognized that a non-vertical axis could be used, and if such were the case the motion of any particles therein would be strongly directed around planes which were perpendicular to the axis of rotation.

The motion imparted to any particulate contaminants which are in the container is a strongly horizontal one. Utilizing this motion the container image is dissected, using a plurality of fiber optic bundles, into a number of vertical columns which extend from the bottom of the container through the top of the liquid meniscus. The columns are further subdivided into a plurality of unit rectangular areas with each unit area being monitored by a different segment of a fiber optic bundle. The illumination value detected by each fiber optic bundle segment is electronically translated into a voltage signal using a constant sensitivity photo sensor. The signals from the photo sensors are processed through a differentiator so that only changes in illumination are recorded. Therefore constant illumination signals from container imperfections, lettering or art work, or a constant saturation signal, where specular reflections are encountered, are not recognized. Any constant sensitivity photo transducer i.e., which generates an output signal which is substantially directly proportional to the illumination value viewed, within its operating range, could be used. By so utilizing a number of vertical columns the image of particulate matter which moves past a column with a saturated sensing means will be detected as it passes through a column with an unsaturated sensing means and a particle which passes through an area obscured due to lettering or art work on the container will be detected as it passes through an unobscured area.

The sensing device consisting of the fiber optic bundles and the array of photo sensors further divides the image of the rotating liquid into block areas which permit the central meniscus volume and the circumferential edge meniscus volume to be separately monitored from the remainder of the rotating liquid. The lower portion of the rotating liquid image, below the maximum meniscus displacement, may be immediately monitored for particulate contamination by the lower unit rectangular areas of the vertical columns, since any changes in illumination occurring in the submeniscus volume image would only be from moving particulate matter. The volume of liquid which contains the center of the meniscus may be monitored shortly thereafter, when it has substantially reached its rest position and the interfering illumination signal which it generates is negligible. This time lag is necessary for small particle identification since the interfering illumination signal which is first generated by the center of the meniscus would make identification of small moving particles virtually impossible, and the meniscus decay correction step as discussed below, if extended to include the entire meniscus could result in an error signal as great as a small moving particle signal.

The circumferential edge of the meniscus which is in contact with the wall of the container is slower to approach its rest position because of the liquid's tendency to adhere to the wall of the container. However, in applicant's improved system, the peripheral edge of the rotating meniscus can also be monitored for particulate contamination by compensating for the interfering illumination signal which is generated by the decaying meniscus as it approaches it rest position.

The peripheral edge of the meniscus will decay with essential uniformity to its rest position, therefore the illumination signal which is generated by the meniscus decay will be substantially uniform along the peripheral edge. Accordingly, if the illumination output signal originating in one of two portions of the meniscus edge, in which the voltage signals generated by the meniscus decay would be substantially similar, is substracted from the illumination output signal originating in the other portion, the interfering output signal due to the meniscus edge decay is substantially eliminated, and any signal which is recorded will be due to particulate movement. The meniscus edges could be monitored in this manner for particulate contamination as soon as the center of the meniscus has substantially reached its rest position as discussed above.

The maximum error signal which results from the meniscus correction step is of small magnitude and can be easily distinguished from the particulate movement signals. If an even greater sensitivity is desired, however, the inspection of the edges can be delayed until shortly after the meniscus center inspection. By waiting this slight additional time, the maximum error signal which can result from the meniscus correction step will be even smaller. Accordingly, particles which generate smaller signals can be monitored.

In the inspection of parenteral solutions for particulate contamination, the preferred embodiment delays the start of the inspection of the meniscus edges until shortly after the start of the inspection of the central meniscus volume. The signal from each photo sensor is amplified as required, summed and differentiated. The differentiated signals indicate whether any change in illumination occurs on each of the unit areas instrumented. Change of unit area illumination after the container is at rest is due to particle movement. The accept/reject decision is based upon the comparison of a standard reference signal to a composite of the magnitude of the differentiated signals, the integral of all such signals, any signal detected over a certain predetermined value or any combination of the above.

DESCRIPTION OF THE PREFERRED EMBODIMENT

Figure 1:
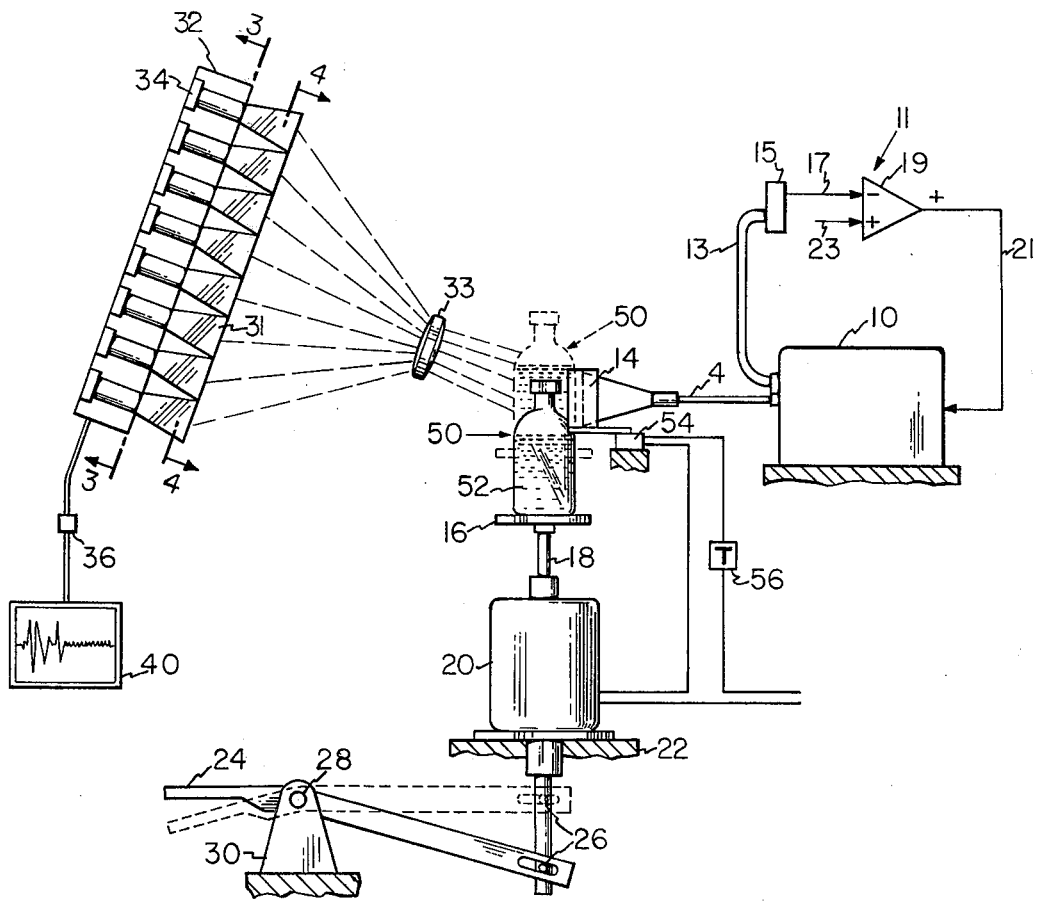
FIG. 1 is a side elevational view of the apparatus showing the array of detectors and the print-out chart.
Figure 2:
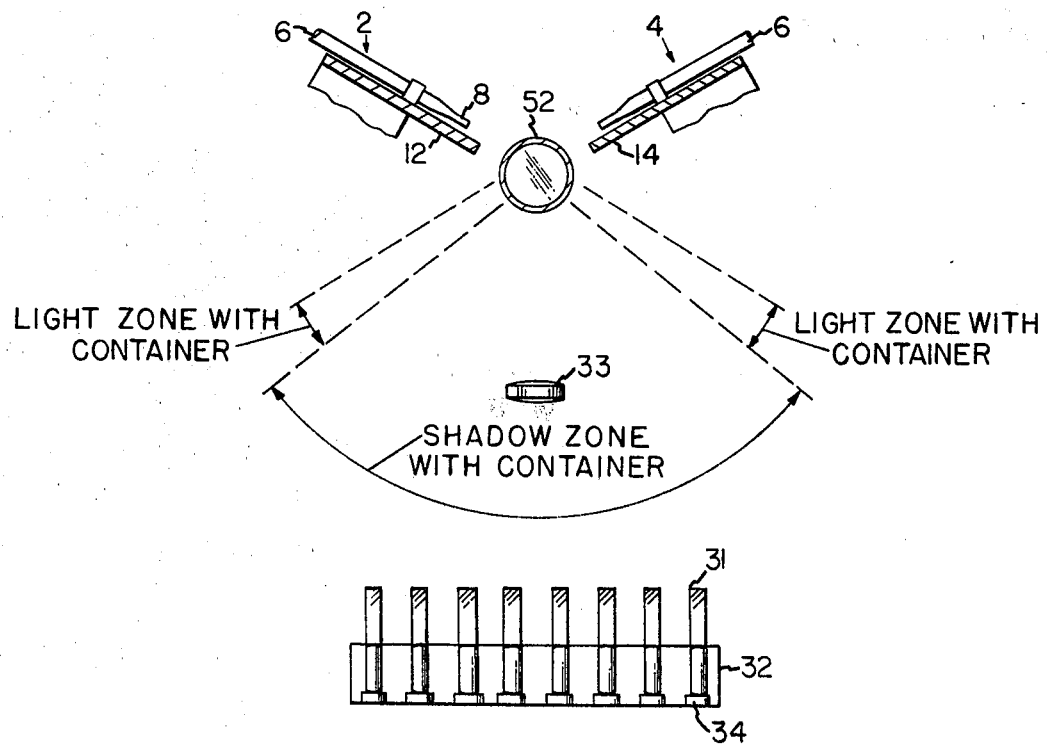
FIG. 2 is an enlarged schematic view showing the passage of light through the container and liquid, with the array of detectors located in the shadow zone.

Referring to FIG. 1 and 2, cables 2, 4 consist of a fiber optic bundle within a protective shield 6. The ends of the cables 2, 4 are open with one end of each connected to a light source 10. The light from the source is transmitted through the fiber optic bundle 8 to the opposite ends of the cables 2, 4 which ends are mounted in fixed position behind the baffles 12, 14. Any light source having an intensity sufficient to illuminate the liquid and particles, and compatible with the viewing means, may be used. A 150 watt 21 volt incadescent lamp, for example, General Electric type EKE, has been found suitable. The light source 10 is maintained at a constant intensity by circuit 11. Circuit 11 consists of a fiber optic light intensity sampler 13 which continually monitors the intensity of illumination of the light source 10, a photo transducer 15 for generating a voltage signal 17 proportional to the light intensity monitored by sampler 13, and a servo amplifier 19 for controlling the current 21 to the lamp 10, based upon a comparison of voltage signal 17 to a stored reference level signal 23.

Turntable 16 is mounted on shaft 18, driven by motor 20 and mounted in a fixed position on support 22. Shaft 18 is movable vertically through the lever 24 pivoted, at 26, to shaft 18 and pivoted, at 28, to fixed support 30. Sealed container 50, containing solution 52, is placed on turntable 16 and the turntable is lifted by depressing lever 24. As turntable 16 and container 50 reach the position shown in phantom lines in FIG. 2, microswitch 54 is closed and, through timer 56, actuates motor 20 for a preset time interval to rotate turntable 16, container 50 and solution 52. The speed and time of rotation is sufficient to cause solution 52 and any particles therein to rotate but is below the speed of cavitation, bubbling and entrapment of air in the solution. Instead of the manual lever system it would, of course, be an obvious expedient and within the scope of this invention to feed the bottles onto the turntable automatically.

At the end of the container spin time, the image of the rotating liquid transmitted by lens 33 is immediately inspected by means of a plurality of downwardly directed fiber optic bundles 31, with each fiber optic bundle 31 being operatively connected to one of the photo sensors 34 of the array of photo sensors 32. Each of the fiber optic bundles are directed to a different unit portion of the rotating liquid, for purposes more apparent hereinafter. Each photo sensor is responsive to an illumination value within its respective unit area which is greater than its constant sensitivity value. All of the signals from the photo sensors are processed through an electronic circuit 36 and the resulting composite output signal is graphically printed at recorder 40. Recorder 40 can be used by an inspector to determine if the particle content of the container is acceptable. Of course, if a completely automatic system is used recorder 40 could be replaced by any standard signal processor which had a stored acceptable criteria for the container under inspection, as will be discussed hereinafter in regards to FIG. 11.

In the method and apparatus of the preferred embodiment of the instant invention, the surface of any particle in the solution is illuminated both by direct and reflected light. The light means directs at least two light beams at the liquid filled container along light paths angularly disposed to the fiber optic bundle viewing axis passing through the container so that the light paths intersect in the container and illuminate substantially all of the liquid and form an angular shadow zone at the fiber optic bundle. This phenomenon is illustrated in FIG. 2 and described in the aforementioned U.S. Pat. No. 3,627,423.

Figure 3:
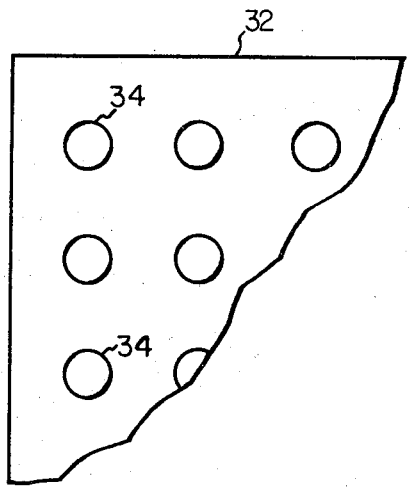
FIG. 3 is a partial sectional taken along the line 3—3 of FIG. 2 showing the array of photo sensors.

FIG. 3 shows a partial cross sectional view of the array of photo sensors 32. Each of the photo sensors 34 would be operatively connected to one of the fiber optic bundles 31.

Figure 4:
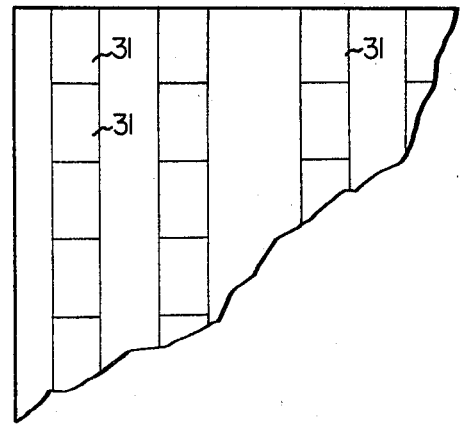
FIG. 4 is a partial sectional taken along the line 4—4 of FIG. 2 showing the optic fiber bundles.

FIG. 4 shows a partial cross sectional view of the fiber optic bundles 31. The bundles are shown to be rectangular at their viewing end although any shape which enabled the container image to be dissected along vertical scan lines could be used. The fiber optic bundles would, of course, be bunched at their opposite ends to conform to the shape of their respective photo sensors 34.

Figure 5:
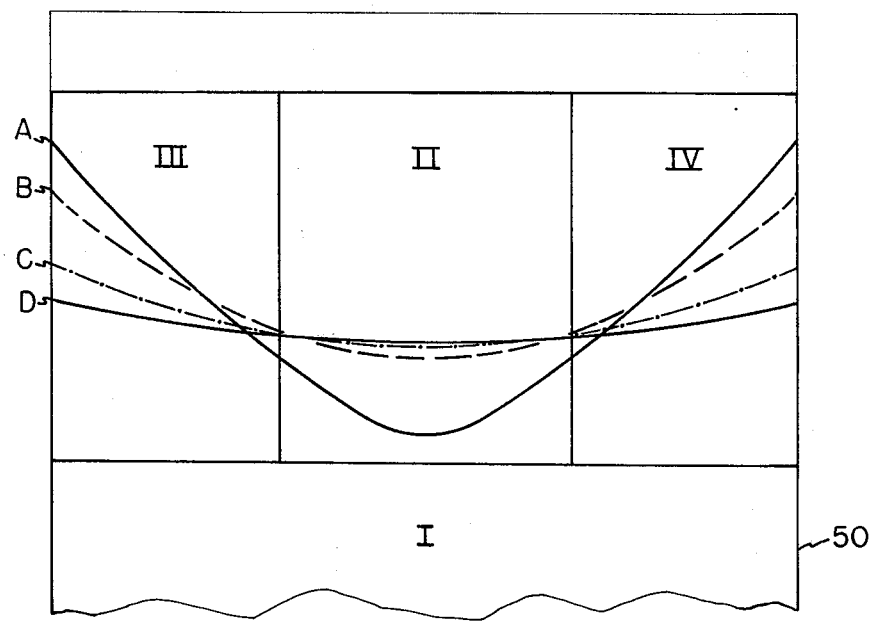
FIG. 5 is a front elevational view of an ampoule showing the maximum meniscus displacement and the meniscus level at different times within the block areas.

FIG. 5 shows the shape of the meniscus at its maximum displacement, at rest, and at various times during the rotation of the liquid in the ampoule. Level "A" is representative of the shape of the meniscus at its maximum depth and level "D" is representative of the shape of the meniscus when the solution is at rest. Levels "B" and "C" are representative of the shape of the meniscus at two intermediate times, with the time interval between levels B and C being approximately the same as the time interval between levels B and A. As can readily be seen from FIG. 5, the center portion of the meniscus very rapidly approaches its rest position when the container spin is stopped, while the edge portions of the meniscus move much slower due to the tendency of the fluid to cling to the walls of the container. As a result of this characteristic of the meniscus decay, the center portion of the meniscus can be monitored soon after the container spin is stopped. However, by using the new improved system of the instant invention, even the meniscus edge areas can be meaningfully monitored for particulate contamination, while the interfering output signal from the decaying meniscus is still relatively large, by compensating for the meniscus decay in a manner hereinbelow described in relation to FIG. 6.

FIG. 5 further shows the four block areas into which the ampoule image is divided by the array of detectors. The blocks are selected so that the ampoule may be inspected even though there are error signals originating from the vortex and the resulting meniscus decay. Block I is the area of the ampoule image which extends downward from a point just below the maximum meniscus displacement to the bottom of the container. Block II is the upper central portion of the rotating liquid volume image and extends from a point above the maximum meniscus creep on the wall of the container downward to the upper edge of Block I. Blocks III and IV are the edge areas of the rotating meniscus image and are positioned above Block I, and are adjacent to an on opposite sides of Block II.

The inspection of the container is started the moment the container spin is stopped. The continuous monitoring of Block I is started immediately since no interfering output signal originates in Block I. Block II is continuously monitored from the time the interfering output signal due to the decay at the meniscus center is negligible, in comparison to the signal which would be generated by the smallest moving particle of interest, e.g. level B. Blocks III and IV will continue to each have a substantial interfering output signal due to the meniscus decay even after the signal from Block II has become negligible. Applicant's new improved system subtracts the signals which are generated in Blocks III and IV from one another. Since the interfering output signal due to the meniscus decay is substantially the same in both blocks, the signal which remains after the subtraction step will be due primarily to particulate movement, although a slight error signal is possible even after the subtraction. The maximum error signal which is possible after the subtraction will decrease as the meniscus further decays, e.g. from level B to level C. Therefore, if an inspection for very small particles is required, it may be necessary to delay the monitoring of Blocks III and IV until the maximum possible error signal after the substraction step is less than the signal which would be generated by the smallest particle of interest.

Figure 6:
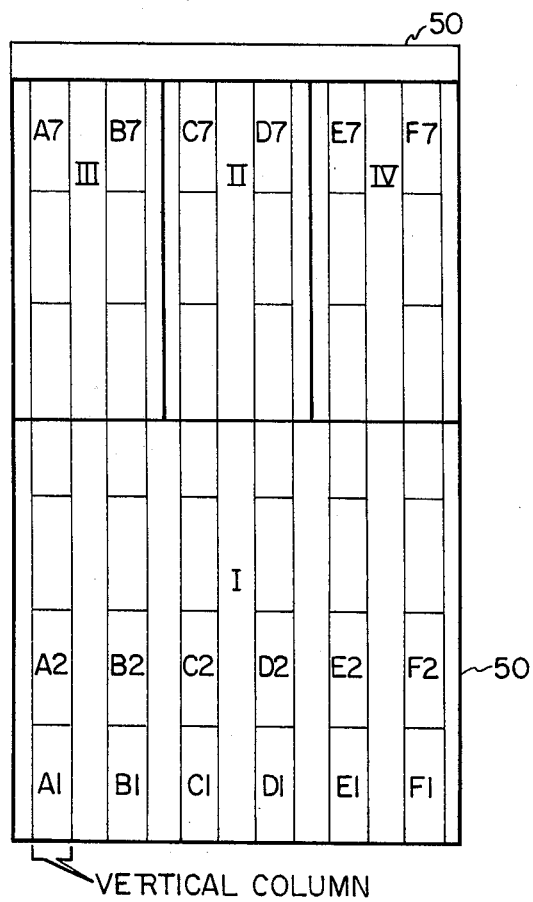
FIG. 6 is a front elevational view of an ampoule showing the relationship of the assigned unit areas, monitored by each photo sensor, within the block areas.

FIG. 6 shows the ampoule block areas further divided into a plurality of vertical columns with each vertical column extending the length of the rotating liquid.

Since the motion which is imparted to each of the contaminant particles is a strongly horizontal one, it is essential that any individual vertical column be monitored along its entire length so as to prevent a particle from going undetected while rotating in an unmonitored zone. Each of the vertical columns are further subdivided into a plurality of unit rectangular areas, e.g. $A_1 \ldots A_7$; $F_1 \ldots F_7$. Each of the rectangular areas are monitored by one of the fiber optic bundles. The fiber optic bundles allow the unit areas to be clearly defined while preventing an unmonitored zone to occur between adjacent vertically spaced rectangular areas.

Since each of the photo sensors is of constant sensitivity, they will record a signal substantially proportional to the illumination viewed. This signal can be the result of either specular reflection from the container, a flaw or mark on the surface of the container, meniscus decay, liquid surface specular reflection, or particulate movement. These signals are further processed through a differentiator so only signal changes are recorded. A composite signal from each of the block areas is then compiled. That is, each block area will generate a composite of all of the differentiated signals coming from that respective block area. Container flaws or marks and specular reflections will generate a constant signal and will not be recorded. When specular reflections are sufficiently large the corresponding photo sensor will saturate at a constant saturation signal which will not be recorded, see FIG. 10. If a photo sensor is saturated, a moving particle which may be present in the respective area will not go undetected, since it will be detected when it passes through an adjacent unsaturated unit rectangular area. The meniscus decay which occurs in Block II will generate a signal but it will be negligible and easily distinguishable from a moving particle signal. The meniscus decay which occurs in Block III will generate a composite differentiated signal which will be very close to the composite differentiated signal from meniscus decay which is generated in Block IV. Subtraction of the composite differentiated signals from Blocks III and IV will therefore compensate for the meniscus decay signal within these Blocks. The remaining composite signal after the subtraction of the signals from Blocks III and IV will indicate only the moving particulate matter present in the meniscus edge. The slight difference in the differentiated signals which may result from the meniscus decay in Blocks III and IV will be negligible and will accordingly be easily distinguishable from any signal resulting from particulate movement. Any number of detectors could be used and this number would, of course, be highly dependent on many factors including both the container size and the degree of particle sensitivity desired.

Figure 7:
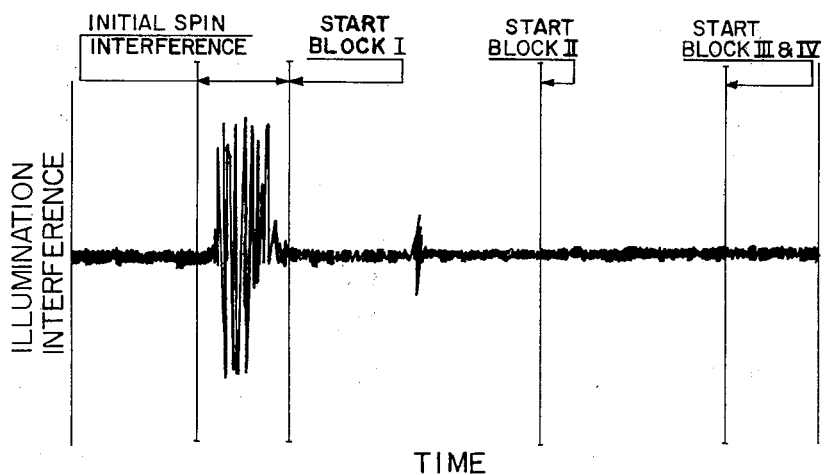
FIG. 7 is a typical graph resulting from a single inspection of an acceptable ampoule which has a very low contamination of small particles.
Figure 8:
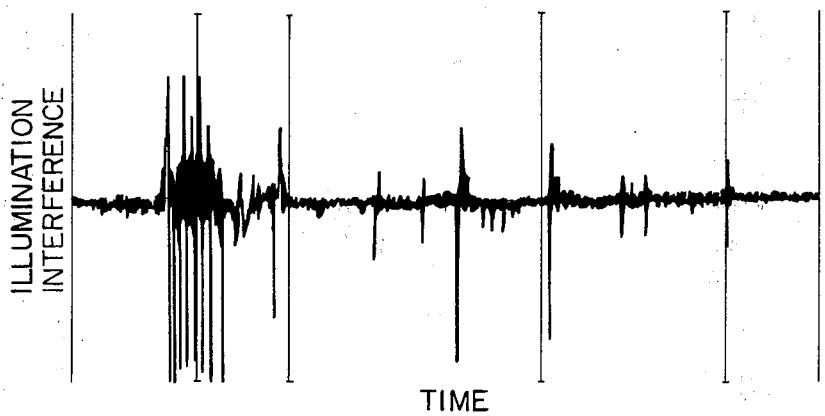
FIG. 8 is an illustrative graph of an unacceptable ampoule having a slight contamination of small particles with a few larger particles.
Figure 9:
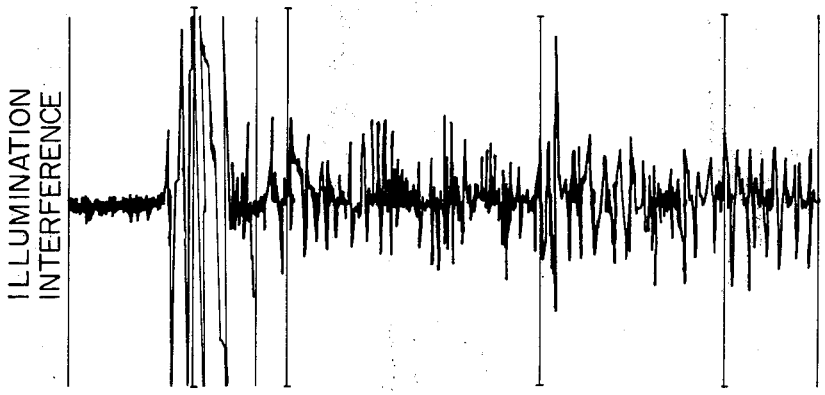
FIG. 9 is a typical graph of an unacceptable ampoule having a high contamination of both small and large particles.

FIGS. 7–9 are schematic view showing the results of a single inspection of an ampoule. As can be seen from the figures, when the ampoule is first spun a considerable amount of interference is detected, but as the spinning liquid approaches its maximum, the interference signal decays to an insignificant noise level. Each signal which is observed after the start of the monitoring time is indicative of a change in illumination resulting from a moving particle, with the height of the peak and the total area of the signal under the peak being indicative of the type and size of the particle observed. For example, a large spherical dark particle will probably generate a short and wide signal, while a small highly reflective particle will probably generate a high, thin signal. Also a large thin particle will generate a signal according to how much of a surface it presents to the photo sensor. If the photo sensor only "sees" its edge then a small signal will be recorded. Since this is a continuous monitoring system these apparently false misrepresentative signals will not go undetected for the large thin particle will be detected when it eventually presents its larger surface to one of the photo sensors. Of course, signals need not be graphically recorded. Any standard signal processor with a stored acceptable criteria which had, for example, an integrator, comparator, peak detector and adder or any combination thereof could be used to accept or reject the container.

Figure 10:
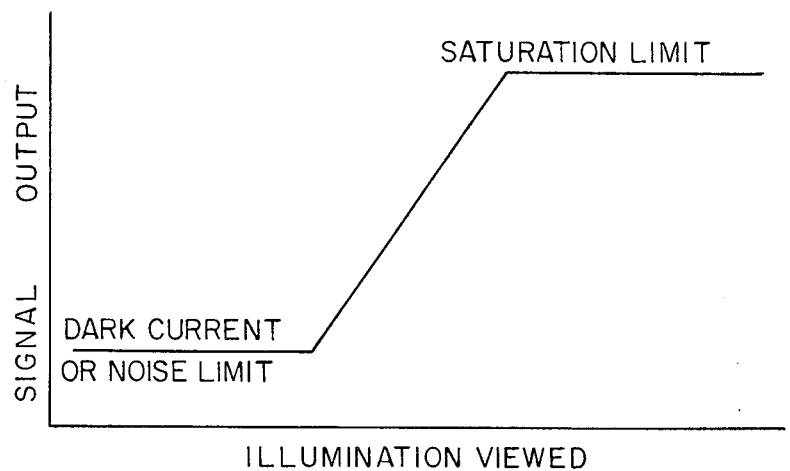
FIG. 10 is a typical graph showing the relationship of the illumination received by a constant sensitivity photo sensor to the signal transmitted by the photo sensor.

FIG. 10 shows a graph of the signal generated by a typical photo transducer vs. the actual illumination viewed in the zone monitored. As can be seen from the graph, the photo transducer will not generate a signal until the illumination is above a certain minimum level called the dark current or noise level. Similarly the photo sensor will saturate at a certain peak illumination and further readings will go undetected. Since a constant sensitivity photo transducer is used, the operating range between the dark current or noise level and the saturation limit results in a substantially straight line.

Figure 11:
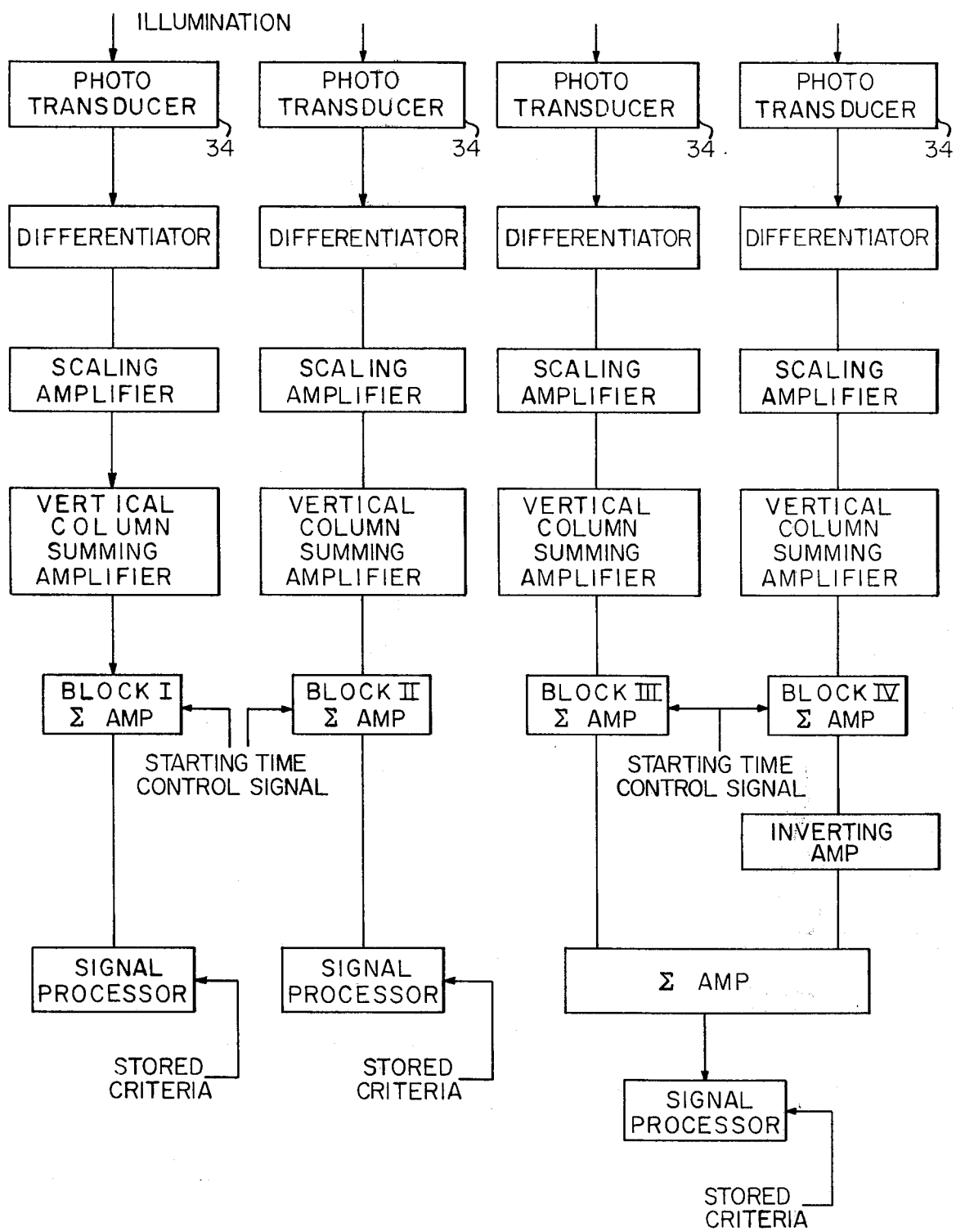
FIG. 11 is a block diagram showing a representative electrical circuit for processing the signals from each of the unit areas.

FIG. 11 shows an electronic circuit 36 which could be used to practice the preferred embodiment of the invention. In FIG. 11 the illumination value within each unit rectangular area, as detected by each fiber optic bundle, is monitored by a single constant sensitivity photo transducer which generates a signal when the illumination is greater than the lower detection limit as shown in FIG. 10. This signal, if any, is then differentiated and amplified. The amplified signals from each unit area are then summed along the vertical column portion within the respective block and the composite summed vertical signals are then summed throughout their respective blocks. Each of the block summing amplifiers are started at the appropriate time, as discussed above, through a control signal. Once the block summing amplifier is operating, it continually amplifies signals which can be processed and compared to a standard acceptable criteria upon which an accept/reject decision can be made. The signal processor can be any known device for that purpose, such as, a comparator for any maximum peak height over a certain level, an integrator for all signals, a peak detector and adder for all signals, or any combination of the above. It is, of course, realized that this electronic circuit could be modified in numerous ways without changing the spirit or scope of the invention. For example, the amplifier could be omitted, the signals could be first summed horizontally, or the differentiation could take place after one of the summing operations.

The invention is not limited to the embodiments described above, but all changes and modifications thereof, not constituting departures from the spirit and scope of the invention are intended to be covered by the following claims.

We claim:
1. A method for inspecting a liquid-filled transparent container, that may have a multiplicity of specular reflections on or in itself, to detect foreign particles in the liquid, said method comprising the steps of:
   a. placing the article at an inspection station,
   b. rotating said liquid about an axis while holding said container stationary,
   c. illuminating said article, d. dissecting the article image into a plurality of columns which extend from the bottom of the container through the top of the liquid meniscus,
e. monitoring each of said columns with separate sensing means for changes in illumination,
f. electronically translating said changes in illumination into voltage signals,
g. forming a composite signal of said voltage signals,
h. comparing said composite signal to a standard reference signal and based thereon accepting or rejecting said article for particulate contamination; whereby the image of particulate matter which moves past a column with a saturated sensing means will be detected as it passes through a column with an unsaturated sensing means.

2. A method as in claim 1 wherein said step of dissecting said article image is accomplished by means of a plurality of fiber optic bundles.

3. A method as in claim 2 wherein said step of monitoring each of said columns is accomplished by monitoring the change in illumination of each of said fiber optic bundles by means of a constant sensitivity photo sensor.

4. A method as in claim 1 wherein said columns are spaced from one another and parallel to said axis of rotation.

5. A method as in claim 1 wherein each of said columns is further dissected into a plurality of unit areas wherein the sub-meniscus volume of the liquid is monitored by the unit areas at one end of said columns and the meniscus volume image is monitored by the remainder of said unit areas.

6. A system for inspecting a liquid filled container for particulate contamination comprising:
a. a source of radiation directed at said liquid filled container,
b. means to rotate said liquid about an axis while said container is held stationary at an inspection station,
c. means to dissect the article image into a plurality of columns which extend from the bottom of the container through the top of the liquid meniscus,
d. sensing means to separately monitor each of said columns to detect changes in illumination,
e. means to translate said changes in illumination into voltage signals,
f. means to form a composite signal of all of said voltage signals.
g. means to accept or reject said liquid filled container based upon a comparison of said composite signal to a standard reference signal.

7. A system as in claim 6 wherein said dissection means dissects the image of said container into a plurality of columns spaced from one another and aligned parallel to said axis 8. A system as in claim 6 wherein said monitoring means is a constant sensitivity photo sensor means.

9. A system as in claim 8 further comprising a means to differentiate the voltage signals from said photo sensor means so that only signal changes will be transmitted therefrom.

10. A system as in claim 6 wherein said source of radiation is a light source of constant intensity.

11. A system as in claim 6 wherein said dissection means is a fiber optic bundle means and said monitoring means is a constant sensitivity photo sensor.

12. A system as in claim 11 wherein said source of radiation comprises a light means for directing at least two light beams at said liquid filled container along light paths angularly disposed to the fiber optic bundle viewing axis passing through said container so that said light paths intersect in said container and illuminate substantially all of said liquid and form an angular shadow zone at said fiber optic bundle.

13. A method for inspecting the meniscus of a rotating liquid in a transparent stationary container for particulate contamination comprising the steps of:
a. illuminating said meniscus,
b. monitoring said meniscus at two portions in which the voltage signals generated by the meniscus decay would be substantially similar for changes in illumination due to moving particulate matter and meniscus decay,
c. electronically translating each of said changes in illumination into a voltage signal,
d. substantially eliminating the voltage signals due to the meniscus decay by electronically subtracting the voltage signals originating in each of said two portions,
e. forming a composite signal of all of said moving particulate matter voltage signals,
f. comparing said composite signal to a standard reference signal and based thereon accepting or rejecting said liquid filled container for particulate contamination.

14. A method for inspecting a liquid filled transparent container for foreign particles in the liquid, said method comprising the steps of:
a. placing the article at an inspection station,
b. rotating said liquid about an axis below the speed that will cause cavitation and bubbling of the liquid while holding said container stationary,
c. illuminating said article,
d. dissecting said rotating liquid volume into a meniscus volume image and a sub-meniscus volume image,
e. monitoring said sub-meniscus volume image for changes in illumination which are indicative of moving particulate matter,
f. monitoring said meniscus volume image at two portions, in which the voltage signals generated by the meniscus decay would be substantially similar, for changes in illumination which are indicative of moving particulate matter and the meniscus decay of the rotating liquid,
g. electronically translating each of said changes in illumination into voltage signals,
h. substantially eliminating the voltage signals due to the meniscus decay by electronically subtracting the voltage signals originating in each of said two portions,
i. forming a composite signal of all of the moving particulate matter signals from said sub-meniscus volume and said meniscus volume,
j. comparing said composite signal to a standard reference signal and based thereon accepting or rejecting said liquid filled container for particulate contamination.

15. A method as in claim 14 wherein said sub-meniscus volume image is monitored from a first time immediately after the rotation of said container is stopped, and said meniscus volume image is monitored from a second time subsequent to said first time.

16. A method as in claim 14 wherein said two meniscus image portions are the two meniscus image edge portions and said meniscus image is further separately monitored at a center portion located between said two edge portions.

17. A method as in claim 16 wherein said sub-meniscus volume image is monitored from a first time immediately after the rotation of said container is stopped, said meniscus center portion image is monitored from a second time subsequent to said first time and said meniscus edge portion images are monitored from a third time subsequent to said second time.

18. A method as in claim 14 wherein said rotating liquid volume image is dissected into a plurality of columns each of which extend from the bottom of the rotating liquid image through the meniscus image of the rotating liquid, each of said columns being further dissected into a plurality of unit areas, wherein said sub-meniscus volume image is monitored by the unit areas at one end of said columns and the meniscus volume image is monitored by the remainder of said unit areas.

19. A method as in claim 18 wherein said unit areas are rectangular.

20. A method as in claim 18 wherein said meniscus volume image and said sub-meniscus volume image monitoring means comprises a plurality of fiber optic bundles, each of which are operatively connected to one of said unit areas.

21. A method as in claim 20 wherein said meniscus volume image and said sub-meniscus volume image monitoring means further comprises a plurality of constant sensitivity photo sensors, each of which are operatively connected to one of said fiber optic bundles.

22. A method as in claim 14 wherein said composite signal comprises a composite of the magnitude of all of said moving particulate matter voltage signals.

23. A method as in claim 14 wherein said composite signal comprises the integral of all of said moving particulate matter voltage signals.

24. A method as in claim 14 wherein said composite signal comprises any moving particulate matter signal detected over a certain predetermined value.

25. A system for inspecting a liquid filled container for particulate contamination comprising:
   a. a source of radiation directed at said liquid filled container,
   b. means to rotate said liquid about an axis while said container is held stationary at an inspection station,
   c. means to dissect the image of said rotating liquid into a meniscus volume image and a sub-meniscus volume image,
   d. means to monitor said sub-meniscus volume image for changes in illumination due to moving particulate matter,
   e. means to monitor said meniscus volume image at two portions, in which the voltage signals generated by the meniscus decay would be substantially similar, for changes in illumination due to moving particulate matter and the meniscus decay of the rotating liquid,
   f. means to electronically translate said changes in illumination into voltage signals,
   g. means to substantially eliminate the voltage signals due to the meniscus decay by electronically subtracting the voltage signals originating in each of said two portions,
   h. means to form a composite voltage signal of all of said moving particulate matter voltage signals,
   i. means to compare said composite signal to a standard reference signal, and means to accept or reject said container based thereon.

26. A system as in claim 25 wherein said means for monitoring said meniscus and said sub-meniscus volume images comprise a plurality of constant sensitivity photo sensors.

27. A system as in claim 25 wherein a fiber optic bundle means is used as the means to dissect the image of the rotating liquid.

28. A system for inspecting in relative size particulate matter in a liquid comprising:
   a. a light source,
   b. means to maintain said light source at a constant intensity,
   c. means to rotate said liquid about an axis while said container is held stationary at an inspection station,
   d. sensing means to monitor only changes in the illumination value of selected portions of said liquid filled container and to translate said changes in illumination into voltage signals,
   e. means to form a composite signal of all of said voltage signals,
   f. means to accept or reject said liquid filled container based upon a comparison of said composite signal to a standard reference signal,
   whereby the intensity of the illumination value reflected by particles of constant reflectivity are always proportionate to the cross sectional area of the particles viewed.

29. A system as in claim 28 wherein said light source is a lamp and said means of part b comprises:
   a means for sensing the illumination intensity of said lamp, and a servo amplifier means to control the current to said lamp based on a comparison of said sensed intensity to a stored criterion.

30. A method for inspecting illuminated articles wherein each of said articles comprise a liquid-filled transparent container, that may have a multiplicity of specular reflections on or in itself, which liquid is to be inspected for the presence of foreign particles, said method comprising the steps of:
   a. placing the article at an inspection station having associated article illuminating means,
   b. rotating said article about an axis to cause any of said foreign particles to rotate in planes substantially parallel to said axis of rotation,
   c. while the illuminated liquid and any particles therein continue to swirl, dissecting the article image into a plurality of columns each of which intersect all of said planes at more than one point,
   d. continuously monitoring with separate sensing means each of said columns to detect changes in illumination,
   e. electronically translating said changes in illumination into voltage signals,
   f. forming a composite signal of said voltage signals,
   g. comparing said composite signal to a standard reference signal and based thereon accepting or rejecting said article for particulate contamination;
   whereby the image of particulate matter which moves past a column with a saturated sensing means will be detected as it passes through a column with an unsaturated sensing means.

31. A method as in claim 11 wherein said article is rotated below the speed that will cause cavitation and bubbling of the liquid.

32. A method as in claim 30 wherein said columns are spaced from one another and parallel to said axis of rotation.

33. A method as in claim 30 wherein said columns extend from the bottom of the container through the top of the liquid meniscus.

34. A method for inspecting a sub-meniscus volume of a rotating liquid within a stationary transparent container to detect particulate contamination, said method comprising the steps of:
   a. placing the article at an inspection station,
   b. rotating said liquid about an axis while holding said container stationary,
   c. illuminating said article,
   d. dissecting said sub-meniscus volume image into a plurality of columns each of which extend from the bottom of the container through the top of said sub-meniscus volume,
   e. continuously monitoring with separate sensing means each of said columns to detect changes in illumination,
   f. electronically translating said changes in illumination into voltage signals,
   g. forming a composite signal of said voltage signals,
   h. comparing said composite signal to a standard reference signal and based thereon accepting or rejecting said article for particulate contamination;
   whereby the image of particulate matter which moves past a column with a saturated sensing means will be detected as it passes through a column with an unsaturated sensing means.

35. A method as in claim 34 wherein said columns are spaced from one another and parallel to said axis of rotation.

36. A method as in claim 34 wherein said columns extend from the bottom of the container to a point just below the maximum meniscus displacement.

37. A method as in claim 34 wherein each of said columns is further dissected into a plurality of unit areas.

* * * * *

UNITED STATES PATENT OFFICE
CERTIFICATE OF CORRECTION

Patent No. 3,966,332    Dated June 29, 1976

Inventor(s) Julius Z. Knapp and John C. Zeiss

It is certified that error appears in the above-identified patent and that said Letters Patent are hereby corrected as shown below:

Column 1, line 20, "3.598,907" should read --- 3,598,907 ---.
Column 12, line 47, "parallel" should read --- perpendicular ---

Signed and Sealed this

Fourth Day of April 1978

[SEAL]

Attest:

RUTH C. MASON
Attesting Officer

LUTRELLE F. PARKER
Acting Commissioner of Patents and Trademarks